(12) United States Patent
Lai (10) Patent No.: US 9,611,199 B2
(45) Date of Patent: Apr. 4, 2017

(54) METHOD OF CALIBRATING AND CORRECTING COLOR-BLEED FACTORS FOR COLOR SEPARATION IN DNA ANALYSIS

(71) Applicant: ANALOGIC CORPORATION, Peabody, MA (US)

(72) Inventor: Ching Ming Lai, Wakefield, MA (US)

(73) Assignee: Analogic Corporation, Peabody, MA (US)

( * ) Notice: Subject to any disclaimer, the term of this patent is extended or adjusted under 35 U.S.C. 154(b) by 0 days.

(21) Appl. No.: 14/867,366

(22) Filed: Sep. 28, 2015

(65) Prior Publication Data
US 2016/0018333 A1 Jan. 21, 2016

Related U.S. Application Data

(62) Division of application No. 13/879,668, filed as application No. PCT/US2010/053346 on Oct. 20, 2010, now Pat. No. 9,040,760.

(51) Int. Cl.
| | | |
|---|---|---|
| G01N 21/64 | (2006.01) | |
| C07C 17/25 | (2006.01) | |
| C07C 17/087 | (2006.01) | |
| C07C 17/20 | (2006.01) | |
| C12Q 1/68 | (2006.01) | |

(52) U.S. Cl.
CPC ............ *C07C 17/25* (2013.01); *C07C 17/087* (2013.01); *C07C 17/20* (2013.01); *C07C 17/206* (2013.01); *C12Q 1/686* (2013.01); *G01N 21/6428* (2013.01); *G01N 21/6486* (2013.01); *G01N 2021/6439* (2013.01); *G01N 2201/061* (2013.01); *Y02P 20/582* (2015.11)

(58) Field of Classification Search
CPC ............... G01N 21/64; G01N 21/6486; C12Q 2537/143; C12Q 1/686; C12Q 2563/107
See application file for complete search history.

(56) References Cited

U.S. PATENT DOCUMENTS

| | | | | |
|---|---|---|---|---|
| 6,863,791 | B1 * | 3/2005 | Liu ................... | G06K 9/00127 204/452 |
| 6,982,029 | B2 * | 1/2006 | McVey ............ | G01N 27/44726 204/450 |
| 2010/0120059 | A1 * | 5/2010 | Yan .................... | G01N 21/6428 435/7.1 |
| 2011/0294675 | A1 * | 12/2011 | Brabetz ................ | C12Q 1/6846 506/7 |
| 2012/0049086 | A1 * | 3/2012 | Sakai .................. | G01N 21/274 250/459.1 |

OTHER PUBLICATIONS

Bishop et al., A Setup System for Compensation: BD CompBeads plus BD FACSDiva Software, 2004, BD Biosciences.*

* cited by examiner

*Primary Examiner* — Marcus Taningco
(74) *Attorney, Agent, or Firm* — Anthony M. Del Zoppo, III; Driggs, Hogg, Daugherty & Del Zoppo, Co. LPA (57) ABSTRACT

A method includes calibrating color bleed factors of optical detector channels of a sample processing apparatus through processing a color bleed calibration substance which includes a plurality of different size fragments replicated from different groups of DNA loci, wherein fragments in a same group are labeled with a same fluorescent dye, and fragments in different groups are labeled with different fluorescent dyes having different emission spectra, wherein the different size fragments are processed during different acquisition times.

14 Claims, 7 Drawing Sheets

METHOD OF CALIBRATING AND CORRECTING COLOR-BLEED FACTORS FOR COLOR SEPARATION IN DNA ANALYSIS

TECHNICAL FIELD

The following generally relates to DNA analysis and finds particular application to color bleed factor calibration for color separation in DNA analysis. However, the following is also amenable to other applications.

BACKGROUND

DNA genotyping is a process of determining the sequence of DNA nucleotides at a generic locus, or at a position on a chromosome of a gene or other chromosome marker. For the purpose of identifying a human, certain generic loci have been selected as the standard markers to characterize the DNA. Each marker is a DNA fragment containing a repetition of a certain nucleotide sequence. Generally, there are 13 cores and several other accepted standard markers by the security authorities. These markers contain short repetitions (e.g., roughly from 5 to 40) of four nucleotides. They are in the class of Short Tandem Repeat (STR) of DNA sequence.

The repetition numbers at these markers varies rather randomly from person to person. The specific form of DNA sequence at a generic locus is called an allele, which provides sufficient differentiation among people. The STR sequence is inherited from parent's DNA. At each marker, there may be two different alleles, one from each parent, and it is called heterozygous. If the alleles from both parents have same STR numbers, it is homozygous. If the alleles of 13 core markers were heterozygous, each person will have 26 different allele numbers. Assume each number is evenly distributed over a range of 10, the likelihood of having two people with the same alleles numbers from these 13 markers is extremely small.

To measure allele numbers, a DNA fragment containing all STR nucleotides and adjacent sections of nucleotides at each locus is copied from the DNA sample, and replicated by a technique called polymerase chain reaction (PCR). The fragment size is measured in the unit of base pairs, where a base pair is the size of a pair of DNA nucleotides. The sample is placed in a capillary of a sample carrier, and the fragments are separate by size through electrophoresis in which same size fragments arrive at a destination at about the same time, and different size fragments arrive at the destination at different times.

A modern apparatus for DNA analysis uses a rigid sample carrier called biochip which contains multiple capillaries in parallel to run multiple samples simultaneously. To detect the fragments, a fluorescent dye is attached to the fragments and the sample is excited by a light source of narrow beam at a fixed spot of the capillary. The fluorescent dye is also called fluorophore, and its attachment to fragments is also said to label the fragments. Following the excitation, fluorescent light is emitted from the dye very much instantaneously, typically within one microsecond.

The sizes of the fragments in a DNA locus are known to be within certain range. It is possible to find a number of loci in which the fragment sizes of a locus do not overlapped with other loci. Furthermore, it is possible to divide the whole set of loci into several groups. In each group, the fragment sizes of a locus are separated from other loci, and it is called a color group. The fragment size is measure in DNA base pairs and it is ranged from 100 to 400 base pairs in the figure. For each color group, a dye with a distinct fluorescent color is attached to the fragments of all loci in the group. Usually, the dye is attached to a molecule called primer at one end of the fragment. The fragments are separated by the electrophoresis process and detected by an optical system as a digital signal. A fragment is detected as a peak in the signal, and the detection time of a peak can be used to determine the fragment size.

Based on the non-overlapping range of the loci in the color group, the measured fragment size identifies the locus of the fragment. With other supporting data, the measured fragment size can be used to identify it as one of DNA fragments in the locus with known STR number. The sample is prepared with multiple dyes with one dye for each color group. When the sample is excited by the light source, the fluorescent light is mixed with multiple colors from these dyes. It is necessary to use optical filter to separate the fluorescent colors. Each filtered fluorescent color is measured in a detection channel as an electrical signal. Typically, a photo-multiplier tube (PMT) or other detectors, such as charge-coupled device (CCD) camera is used in each detection channel.

Ideally, the emission spectrum of each dye is narrow such that the spectra of the multiple dyes in the sample do not overlap each other. If that were the case and if the optical filter could also be narrow band to detect only one dye, then each of the detected signals would contain only one dye color. In this hypothetic ideal case, each signal measures one and only one color group, in which a DNA fragment peak would only appear in one of the detected signals. By finding and identifying the peaks in these signals, the complete set of STR numbers in all loci of interest can be determined.

However, the emission spectra of the dyes overlap with each other substantially. As the result, each detected signal contains fluorescent signals from all dyes. This has been referred to as color-bleed, and is similar to the cross-talk problems in electronic instruments. With conventional systems, the degrees of color-bleed can be severe, and it is necessary to know the degree of color-bleed from each dye as accurate as possible. The degree is used as a set color-bleed factors that are used to determine signals corresponding to only one distinct color from a dye through a process referred to as color separation. Unfortunately, an inaccurate set of color-bleed factors can lead to false peaks and/or amplitude-diminished true peaks, which may lead to uncertainty with determining STR numbers.

SUMMARY

Aspects of the application address the above matters, and others.

In one aspect, a method includes calibrating color bleed factors of optical detector channels of a sample processing apparatus through processing a color bleed calibration substance which includes a plurality of different size fragments replicated from different groups of DNA loci, wherein fragments in a same group are labeled with a same fluorescent dye, and fragments in different groups are labeled with different fluorescent dyes having different emission spectra, wherein the different size fragments are processed during different acquisition times.

In another aspect, a method includes generating a first signal indicative of a reference gain of optical detectors of a sample processing apparatus based on a first emission from a gain-monitoring material of the sample processing apparatus in response to illuminating the material, generating a second signal indicative of a subsequent gain of the optical detectors based on a second emission from a gain-monitoring material in response to illuminating the material, and scaling at least one of color bleed factors of the sample processing apparatus or data acquired by the sample processing apparatus based on a signal indicative of a difference between the reference gain and the subsequent gain.

In another aspect, a sample processing system includes a sample carrier receptacle configured to receive a sample carrier carrying one or more samples to be processed by the sample processing system. The sample processing system further includes one or more processing stations for processing the one or more samples. The sample processing system further includes a reader, including an illumination source and one or more optical detector channels, that evaluates separated fragments of a processed sample based on emission spectrums of dyes attached to the fragments, and that generates an output signal. The sample processing system further includes a color separator that color separates a reader output signal corresponding to a processed DNA sample based on color bleed factors of the one or more optical detector channels. The sample processing system further includes a color bleed factor generator and/or corrector configured to determine color bleed factors for the optical detector channels based on processing a color bleed calibration substance, wherein the color bleed calibration substance includes a plurality of different size fragments in which different size fragments are grouped and labeled with different dye having different emission spectrums in different groups, and the different size fragments are processed and detected over different acquisition times.

In another aspect, a sample processing system includes a sample carrier receptacle configured to receive a sample carrier carrying one or more samples to be processed by the sample processing system. The system further includes one or more processing stations for processing the one or more samples. The system further includes a gain-monitoring device that emits light or a gain-monitoring material that emits fluorescent light with a wide spectrum. The system further includes a reader, including an illumination source and one or more optical detector channels, that evaluates the gain-monitoring material and separated fragments of a processed sample based on emission spectrums of dyes attached to the fragments, and that generates an output signal. The system further includes a color separator that color separates an output signal of the reader corresponding to a processed DNA sample based on color bleed factors of the one or more optical detector channels. The system further includes a color bleed factor generator and/or corrector configured to determine a gain of the detector channels based on the signal emitted by the gain-monitoring material and correct the color bleed factors for changes in gain of the optical detector channels.

In another aspect, a color bleed calibration substance includes a plurality of different size DNA fragments in which fragments of the same locus are prepared and labeled with the same fluorescent dye and the different size fragments are processed during different acquisition times by a sample processing system, wherein emission of the fluorescent dyes in response to being illuminated provides a signal in indicative of color bleed factors of detection channels of an optical reader of the sample processing system.

Those skilled in the art will recognize still other aspects of the present application upon reading and understanding the attached description.

BRIEF DESCRIPTION OF THE DRAWINGS

The application is illustrated by way of example and not limitation in the figures of the accompanying drawings, in which like references indicate similar elements and in which.

DETAILED DESCRIPTION

Figure 1:
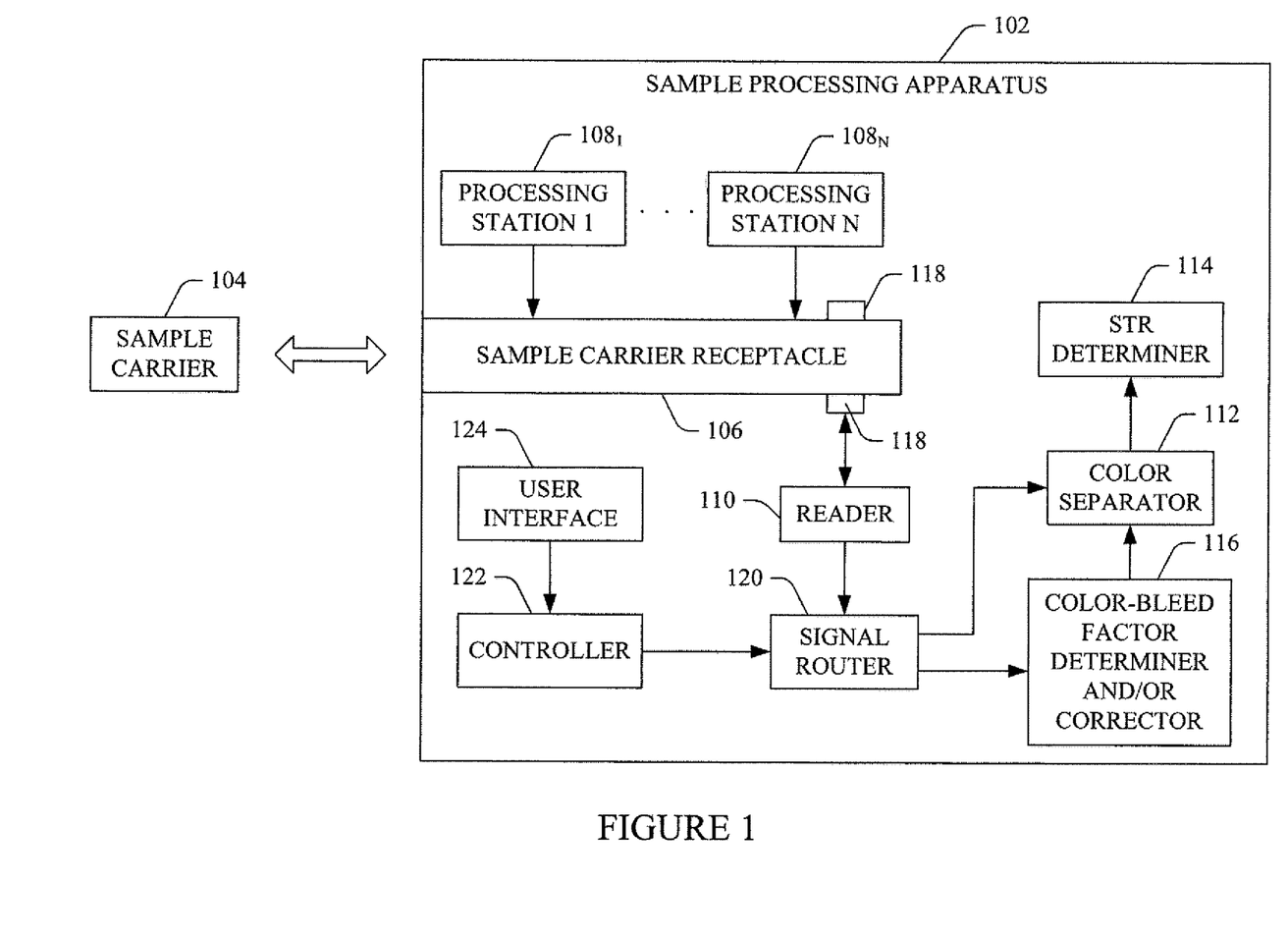
FIG. 1 illustrates an example sample processing apparatus.

FIG. 1 illustrates a sample processing apparatus 102.

The illustrated apparatus 102 is configured for processing one or more samples carried by a sample carrier 104. A suitable sample carrier 104 includes, but is not limited to, a biochip, a lab-on-a-chip, and/or other sample carrier. Such a sample carrier 104 may include one or more micro-channels for carrying and moving, in parallel and/or in series, one or more samples through a plurality of different processing regions of the sample carrier 104. Suitable samples include, but are not limited to, a bio-sample (e.g., saliva, blood, skin cells, and/or other bio-material), a non-bio sample, etc. The sample processing apparatus 102 includes a sample carrier receptacle 106 configured to receive the sample carrier 104.

The sample processing apparatus 102 further includes one or more processing stations $108_1, \ldots, 108_N$ (wherein N is an integer equal to or greater than one), collectively referred to herein as processing stations 108. The illustrated sample processing apparatus 102 is configured to process samples carried by the sample carrier 104 received by the sample carrier receptacle 106. In one instance, such processing includes processing DNA samples carried by the sample carrier 104. In this instance, the processing stations 108 are configured to such functions as extract and purify DNA fragments, replicate and label the DNA fragments with fluorescent dyes having known emission spectrums (or colors), separate the labeled fragments based on fragment size, for example, via electrophoresis, and detect the fragments based on the emission spectrum of the dyes.

The sample processing apparatus 102 also includes an optical reader 110. The reader 110 includes a light source that directs a light beam of a predetermined wavelength range at the separated fragments. In one instance, the light source emits a relatively narrow light beam with a diameter in the order of 10 to 100 microns. In another instance, the light source emits a light beam with a smaller or large diameter. Examples of suitable light sources include, but are not limited to, a laser, a light emitting diode (LED), and the like. The reader 110 also includes an optical detection channel (e.g., a photo-multiplier tube (PMT), a charge-coupled device (CCD) camera, or the like) for each wavelength range (or color) of interest that generates an electrical signal in proportion to the intensity of the fluorescence light within the wavelength range.

A color separator 112 color-separates the signals from the reader 110 based on a set of color bleed factors. Generally, the emission spectra of the dyes attached to the fragments overlap. As the result, the output signal of a detection channel not only will include peaks corresponding to the wavelength of interest of the detection channel, but also possibly peaks from wavelengths of the one or more of the other detection channels. The set of color-bleed factors describes the degree of color-bleed and is used to correct the signals so that each signal measures only one distinct color from a dye. A STR determiner 114 identifies the peaks in the signals and determines STR (Short Tandem Repeat) numbers in loci of interest based on the identified peaks.

A color bleed factor determiner and/or corrector 116 can be used to generate an initial set of color bleed factors and/or, subsequently, a correction thereto before, during and/or after processing a sample. In one instance, the correction compensates for changes in detector channel gain over time. As described greater detail below, the color bleed factors can be determined based on processing a color bleed substance, and the correction thereto can be determined based on processing the color bleed substance, a positive control sample having characteristics of the color bleed substance, and/or one or more gain-monitoring fixtures 118.

A signal router 120 routes the output of the reader 110 to the color separator 112 and/or the color-bleed factor generator and/or corrector 116 based on a mode of operation. A controller 122 generates a signal indicative of a selected mode of operation and conveys the signal to the signal router 120, and the router 120 routes the signal based on the signal. A user interface 124 allows a user of the apparatus to select the mode of operation. Examples of modes include a DNA processing mode, a calibration mode, such as a pre run time, run time, and/or post run time calibration mode, and/or one or more other modes.

It is to be appreciated that the sample processing apparatus 102 may be configured to be a portable apparatus that can be readily moved from location to location. In another embodiment, the sample processing apparatus 102 is configured to be a stationary apparatus mounted to or placed on a table, the floor, etc. in a laboratory, office, or the like and configured to remain at a particular location.

As briefly discussed above, the color bleed factor determiner and/or corrector 116 can be used to determine a set of color-bleed factors. In one instance, the color bleed factor determiner and/or corrector 116 determines the set of color bleed factors based on processing a calibration substance. This is illustrated through FIGS. 2, 3, 4 and 5.

Figure 2:
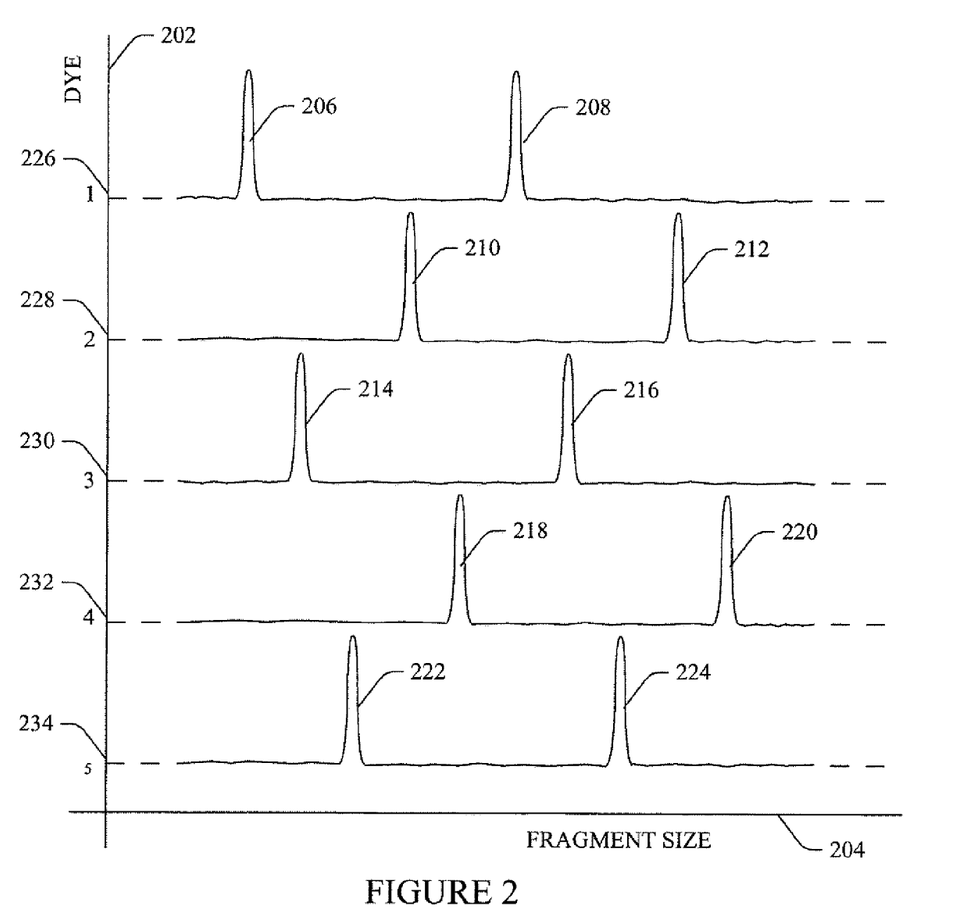
FIG. 2 illustrates an example sub-portion of a distribution of a color bleed calibration substance.

FIG. 2 shows a sub-portion of a color bleed calibration substance as a function of dye (color) and fragment size with five different dyes, each having a different emission spectrum range. A y-axis 202 represents the dyes and an x-axis 204 represents fragment size, and fragments 206 and 208, 210 and 212, 214 and 216, 218 and 220, and 222 and 224 respectively correspond to dyes 226, 228, 230, 232, and 234. The different size fragments are replicated from DNA loci of interest, and fragments in a same group are labeled with a same fluorescent dye, and fragments in different groups are labeled with different fluorescent dyes. Note that the fragments for the different dyes do not overlap in fragment size.

In another example, the color bleed calibration substance includes less than five dyes, and multiple substances are concurrently utilized. In yet another example, a positive control sample with known fragments sizes can be used as the color bleed substance if the positive control sample does not include same size fragments labeled with different dyes. It is to be appreciated that the color bleed calibration substance can also be used as a positive control sample.

Figure 3:
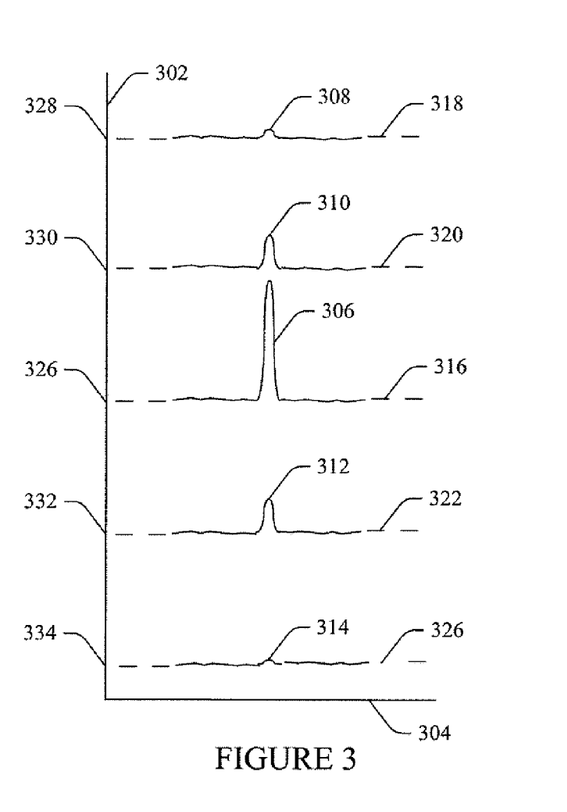
FIG. 3 illustrates an example of color bleed of a dye across optical detectors.

FIG. 3 shows the output of five detection channels of the reader 110 (FIG. 1) for the fragment size 214 attached with dye 230 of the calibration substance of FIG. 2. A y-axis 302 represents detector channel output and an x-axis 304 represents the acquisition time in which the fragment 214 is processed. In this example, peak 306 represents the output 316 of detector channel 326, which is the detector channel configured to detect the emission of the dye 230 attached to the fragment size 214. Peaks 308, 310, 312 and 314 represent the outputs 318, 320, 322 and 326 of the other detector channels 328, 330, 332 and 334, which detect fractional amounts of the emission of the dye 230.

Figure 4:
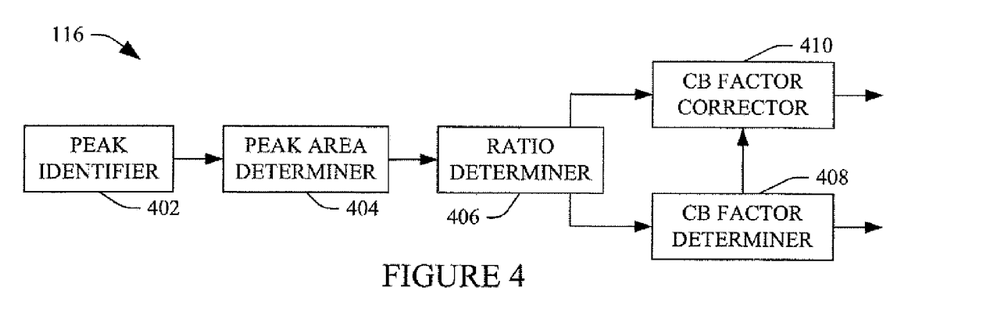
FIG. 4 illustrates an example color bleed factor determiner for determining and/or correcting color bleed factors based on a calibration substance.
Figure 5:
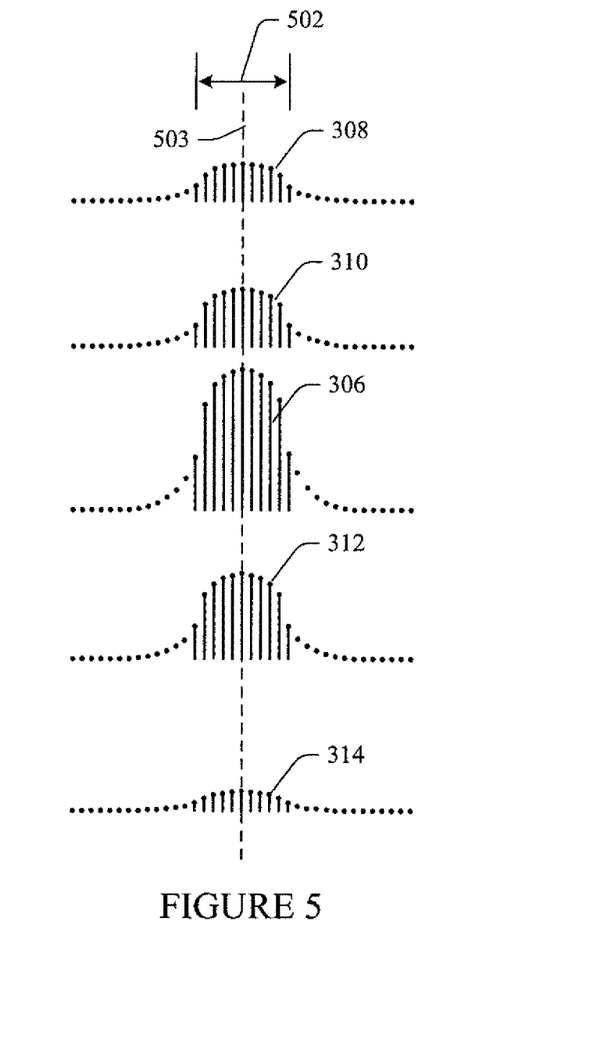
FIG. 5 illustrates an example of determining peak areas for determining color bleed factors.

FIG. 4 illustrates an example color bleed factor determiner and/or corrector 116 used to determine a set of color-bleed factor based on the output peaks 306, 308, 310, 312 and 314 in FIG. 3. A peak area determiner 404 determines an area of each identified peak based on a pre-defined width of the peaks. The pre-defined width may correspond to the entire area of each peak or a sub-portion thereof, such as a width at half the height of the peaks. Using a wider width may increase the signal-to-noise ratio. FIG. 5 shows a magnified view of the peaks 306, 308, 310, 312 and 314 of FIG. 3, an example range 502 for determining peak area, and an axis 503 extending through a maximum height of the peaks.

Returning to FIG. 4, a ratio determiner 406 determines ratios of the areas of the peaks 308-314 to the area of the peak 306, which corresponds to the detector channel for the dye 230. A color bleed (CB) factor determiner 408 determines a set of color bleed factors for the detector channels based on the ratios. For the initial set of color bleed factors, this may performed during a factory calibration before the apparatus 102 is used to process samples. A color bleed (CB) factor corrector 410 determines a correction for color bleed factors, which were previously determined by the color bleed factor determiner 408 and/or otherwise, due to any detector channel gain changes over time. The correction determination may be performed before, concurrently with and/or after processing a sample.

Figure 6:
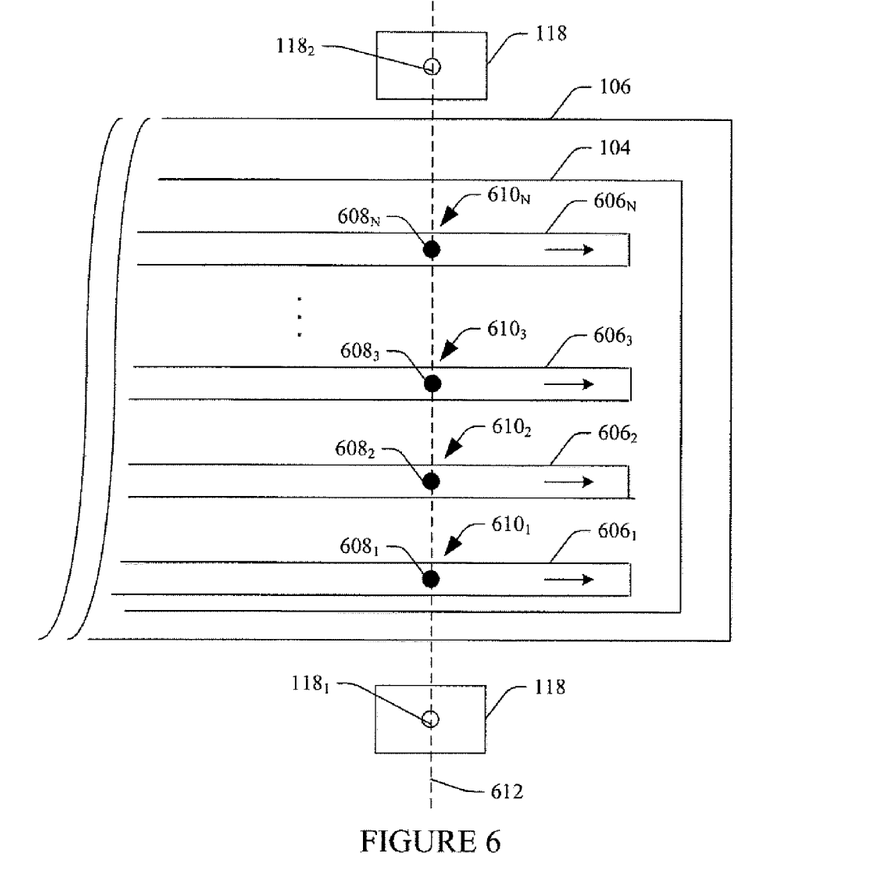
FIG. 6 illustrates an example of the one or more gain-monitoring fixtures in connection with the sample processing apparatus.

As briefly discussed above, the color bleed factor determiner and/or corrector 116 can additionally or alternatively determine the correction to the color bleed factors based on one or more gain-monitoring fixture 118. FIG. 6 shows an example of the one or more gain-monitoring fixture 118 in connection with a sub-portion of the sample processing apparatus 102.

In the illustrated embodiment, the sample carrier 104 is located in the sample carrier receptacle 106, and the sample carrier 104 includes sample channels $606_1$, $606_2$, $606_3$, . . . , and $606_N$ with separated fragments $608_1$, $608_2$, $608_3$, . . . , $608_N$ positioned at reading regions $610_1$, $610_2$, $610_3$, . . . , and $610_N$ located along a reading path 612. The optical reader 110 (FIG. 1) sequentially processes (i.e., illuminates and detects emissions from) the fragments 608 at the reading regions 610.

In the illustrated embodiment, gain-monitoring fixtures $118_1$ and $118_2$ include rigid, transparent, and stabile material such as a plastic or the like that emits wavelengths in a predetermined range in response to being illuminated by the optical reader 110. In one instance, the gain-monitoring fixtures $118_1$ and $118_2$ include one or more pieces of fluorescent plastic implanted or otherwise affixed to the one or more gain-monitoring fixtures 118.

The gain-monitoring fixture $118_1$ is located adjacent to the reading region $610_1$ and on the reading path 612 and the gain-monitoring fixture $118_2$ is located adjacent to the reading region $608_N$ and on the reading path 612. With this configuration, the optical reader 110 can processes the gain-monitoring fixture $118_1$ (or $118_2$), then, sequentially, the fragments 608 at the reading regions 610, and then the other gain-monitoring fixture $118_2$ (or $118_1$).

In another embodiment, the one or more gain-monitoring fixtures $118_1$ and $118_2$ may additionally or alternatively be processed between processing the fragments 608 at the reading regions 610. In yet another embodiment, the one or more gain-monitoring fixtures 118 may additionally or alternatively be processed before and/or after processing any of the fragments 608 at the reading regions 610 or any of the samples carried by the sample carrier 104.

In another embodiment, the one or more gain-monitoring fixtures 118 are omitted and/or included as part of the sample carrier 104. In another embodiment, an additional gain-monitoring fixture(s) 118 is included, for example, as part of the sample carrier (e.g., between channels) and/or as part of the sample processing apparatus 102.

Additionally or alternatively, the sample processing apparatus 102 includes one or more gain-monitoring light sources that emit a spectrum covering a predetermined spectrum such as the emission spectrum of the dyes. The gain-monitoring light source is located in the apparatus 102 such that the signal emitted therefrom is detected by the optical reader 110, and does not have to be by the sample carrier or along the path 612.

Similar to the gain monitoring fixtures $118_1$ and $118_2$, the gain-monitoring light source can be used to determine initial and subsequent detector gains used to determine the gain correction factor. An example of a gain-monitoring light source is a wide-spectrum light emitting diode (LED) that is switched on and off. Another example of such a gain-monitoring light source includes a plurality of different color LEDs covering the emission spectra of the dyes concurrently emit.

Figure 7:
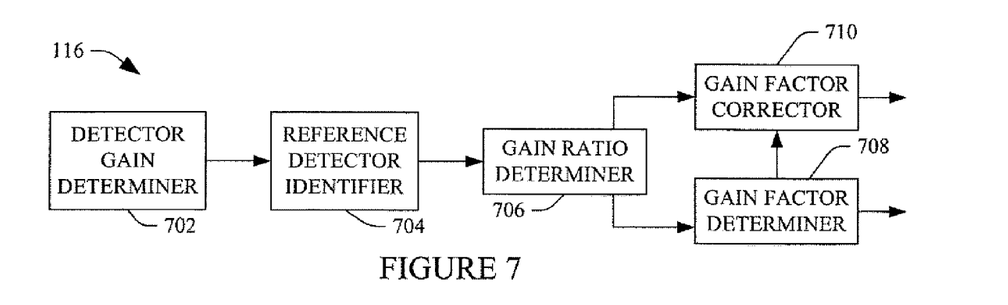
FIG. 7 illustrates an example color bleed factor determiner for correcting color bleed factors based on emissions from one or more gain-monitoring materials or light source.

FIG. 7 illustrates an example color bleed factor generator and/or corrector 116 for correcting color bleed factors based on emissions from the one or more gain-monitoring fixtures 118, or gain-monitoring light sources, detected by the reader 110.

A detector gain determiner 702 determines a gain of each of the detector channels of the optical reader 110. In general, the amplitude of each acquired signal is proportional to the gain of the respective detection channel, after subtracting an offset. If the gain is treated as constant for the run, then the gain can be calculated as the average amplitude of the signal. If the signal is considered to vary with time during the run, then the gain can be fit to a polynomial function.

A reference detector identifier 704 identifies one of the detectors as a reference detector. A gain ratio determiner 706 determines a ratio of the gain of each of the detectors to the gain of the reference detector. A gain factor determiner 708 determines an initial gain factor for the detection channels based on the ratios. These ratios may be saved as reference gain ratios during factory calibration of the apparatus 102.

A gain factor corrector 710 corrects a previously determined detector channel gain for relative detector channel gain changes over time. In the illustrated embodiment, this includes utilizing ratios subsequently determined before, during and/or after processing a sample, and adjusting one or more of the color bleed factors, output of the optical reader 110 before color separation or the color separated signal based on a change between the subsequently determined ratios and the reference gain factor.

Figure 8:
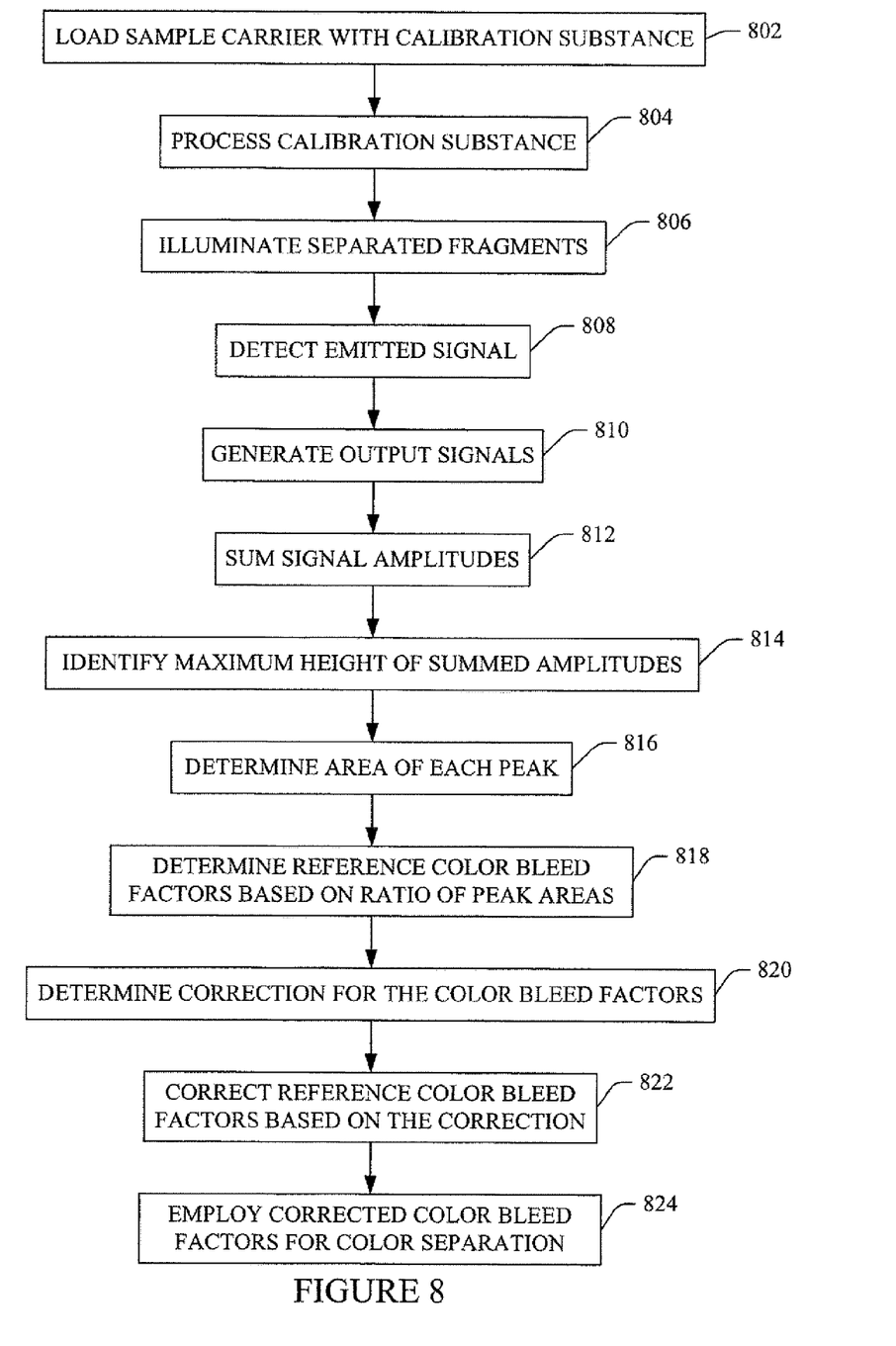
FIG. 8 illustrates an example method for determining and/or correcting color-bleed factors based on a calibration substance.

FIG. 8 illustrates a method for determining and/or correcting color-bleed factors based on a calibration substance.

At 802, a sample carrier carrying a color bleed calibration substance is loaded in the apparatus 102. As described herein, a suitable color bleed calibration substance includes a plurality of different size fragments in which the fragments are divided into multiple groups to be labeled with a distinct dye for each group.

At 804, the calibration substance is processed by the processing stations 108. This includes separating fragments thereof based on fragment size.

At 806, the separated fragments are illuminated with a light source.

At 808, emissions in response to the illumination are detected and processed by a plurality of detector channels, each channel being configured to detect a signal corresponding to the ideal non-overlapping spectrum of a different dye.

At 810, each channel generates an output in which the signal amplitude indicates the amount of the emitted signal detected.

At 812, the signal amplitudes from all the channels are summed for each acquisition time.

At 814, a maximum height of summed signal is identified, and it indicates the presence and the center of a peak generated from a fragment.

At 816, a peak area for each of the individual channel outputs for each acquisition time is determined based on corresponding identified peaks and a predefined acquisition-time range around the peak center.

At 818, a reference color bleed factor for each of the detectors for each of the dyes is generated based on a ratio of the peak areas in the output of the detectors for a dye to the peak area in the output of the detector corresponding to the dye.

At 820, a correction factor for the set of color bleed factors is determined before, during, and/or after processing a DNA sample.

At 822, the reference color bleed factors are corrected, if needed, based on the correction factor.

At 824, the corrected reference color bleed factors are utilized to color separate mixed signals corresponding to processed DNA samples.

Figure 9:
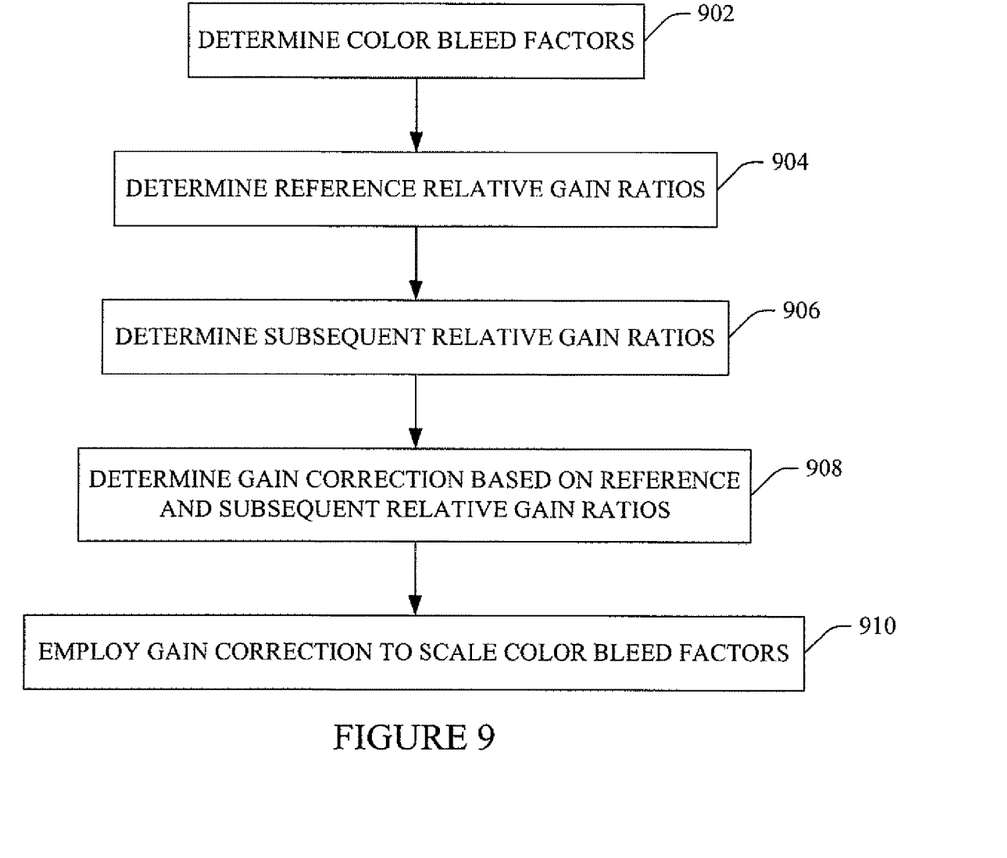
FIG. 9 illustrates an example method for correcting color-bleed factors based on emission from one or more gain-monitoring materials or light source.

FIG. 9 illustrates a method for correcting color-bleed factors based on emission from one or more gain-monitoring fixtures and/or a light-emitting device.

At 902, color bleed factors for each of the detectors for each of the dyes are determined. In one instance, the color bleed factors are determined using a calibration substance as described herein.

At 904, reference relative gain ratios are determined for the detectors using the one or more gain-monitoring fixtures and/or the light source.

At 906, before, during and/or after an acquisition time, subsequent relative gain ratios are determined for the detectors using the one or more gain-monitoring fixtures and/or the light source.

At 908, a gain correction is determined based on the reference relative gain ratios and the subsequently determined relative gain ratios.

At 910, the gain correction is employed to scale one of the color bleed factors. Alternatively, the gain correction is used to scale the output signals of the optical reader 110 before the color separation.

It is to be appreciated that the methods herein can be implemented via one or more processor of one or more computing systems executing one or more computer readable and/or executable instructions stored on computer storage medium such as memory local to or remote from the one or more computing systems.

The following describes embodiments herein in mathematical terms.

The fluorescent light intensity from dye i is $X_i$ and the light intensity detected through detector channel j is $Y_j$. The acquired signal from each detection channel contains substantial amount of offset and certain amount of background signal. The background signal is mostly the excitation light scattered by the biochip material surrounding the capillary. The amount of these offset and background signal are fairly constant throughout the data acquisition, and can be calculated and used for baseline correction. The variable $Y_j$ is the signal amplitude after the baseline has been subtracted from the acquired signal.

For an example with five (5) dyes and five (5) detection channels, the detected signal for channel j can be written as the combination of fluorescent light from five (5) dyes as shown in Equation 1:

$$Y_j = A_{j1}*X_1 + A_{j2}*X_2 + A_{j3}*X_3 + A_{j4}*X_4 + A_{j5}*X_5. \quad \text{Equation 1:}$$

The coefficient $A_{ji}$ can be considered as the color-bleed factor from dye i to detection channel j, if i is not the same as j. For the case of i=j, the coefficient $A_{ii}$ represents the detection efficiency of a dye by its principle channel. It is the principle coefficient, which has the largest value.

The color bleed effect can be described through Equation 2:

$$Y_j = \sum_{i=1}^{5} A_{ji} * X_i \text{ with } j = 1, 2, \ldots, 5. \quad \text{Equation 2}$$

If X is the vector of the dye emission intensities, Y is the vector of the detected signal amplitudes, and A is the matrix of the color-bleed factors, the foregoing can be written as a matrix operation as shown in Equation 3:

$$Y = AX. \quad \text{Equation 3:}$$

It describes the relationship between the dye emission intensity and the detected signal amplitude in a set of simultaneous equations. The unknown dye emission intensity X can be solved by using the inverse matrix of A., as shown in Equation 4:

$$B = A^{-1}. \quad \text{Equation 4:}$$

Then, the dye emission intensity X is given by Equation 5:

$$X = BY, \quad \text{Equation 5:}$$

and in expanded terms as show in Equation 6:

$$X_i = \sum_{j=1}^{5} B_{ij} * Y_j. \quad \text{Equation 6}$$

While the color-bleed factors $A_{ji}$ are all positive values, the inverse matrix coefficients $B_{ij}$ can be positive and negative values. In one instance, it is positive for the diagonal elements and mostly negative for the other elements. The calculation for the dye emission intensities can be considered as de-convolution of the detected signal amplitudes.

If the peak is originated from a fragment attached with dye i, the peak area is denoted as $P_{ji}$ for the color signal j. The peak area $P_{ji}$ measures the fluorescent light intensity emitted by fragments of same size with dye i and detected by the detector channel j under certain scale.

According to Equation 1, it is actually measuring the color bleed factor $A_{ji}$. It is different from $A_{ji}$ only by a scaling factor $s_i$. This scaling factor depends on the amount of fragments attached with dye i. as shown in Equation 7:

$$P_{ji} = s_i * A_{ji}. \quad \text{Equation 7:}$$

If there are m different fragment sizes attached with dye i, the variable k can be used as the index of the fragment size, with k range from 1 to m, rendering Equation 8:

$$P_{ji}(k) = s_i(k) * A_{ji}. \quad \text{Equation 8:}$$

The peak areas generated by all fragments in the color signal with dye i and detected by detector channel j are summed to yield Equation 9:

$$Q_{ji} = \sum_{k=1}^{m} P_{ji}(k). \quad \text{Equation 9}$$

The sum of $s_i(k)$ can be represented as shown in Equation 10:

$$R_i = \sum_{k=1}^{m} s_i(k). \quad \text{Equation 10}$$

Combining the above equations, renders Equation 11:

$$Q_{ji} = R_i * A_{ji}. \quad \text{Equation 11:}$$

Now, based on above equation, the ratio of the coefficient $A_{ji}$ against the principle coefficient $A_{ii}$ can be calculated as shown in Equation 12:

$$A_{ji}/A_{ii} = Q_{ji}/Q_{ii}. \quad \text{Equation 12:}$$

The above equation is applicable for indices i and j. $A_{ii}$ represents the fraction of the fluorescent light from dye i that is detected by the detector channels i. It depends on the emission spectrum of dye i as well as the filtering spectrum of the detector channel i. It can be calculated from the theoretical basis or measured.

A preferred procedure is to start with an estimated fraction (less than one) as the basis to calculate the other coefficients $A_{ji}$ according to above equation. These preliminary values are then used to normalize them such that the sum of these coefficients becomes 1. Let the normalized principle coefficient be $c_i$, the color-bleed factors can be expressed as shown in Equation 13:

$$A_{ji} = c_i * (Q_{ji}/Q_{ii}) \text{ with } i,j=1, 2, 3, 4, 5, \ldots \quad \text{Equation 13:}$$

In summary, based on the signals acquired from the color-calibration substance, the peak areas of the known fragments for each dye i are calculated and summed for each color signals j as $Q_{ji}$. From these values of $Q_{ji}$, the color-bleed factors, or a matrix coefficients $A_{ji}$, can be calculated using Equation 13.

The color-bleed factors may depend on the position of the excitation spot. As such, they can be represented as a function of position along an excitation axis $\lambda$ as $A_{ji}(\lambda)$. At the center spot position, $\lambda=0$, and the color-bleed factors become $A_{ji}(0)$. The position dependent color-bleed factors can be written as shown in Equation 14:

$$A_{ji}(\lambda)=(1+\delta_j(\lambda))A_{ji}(0) \text{ with } i,j=1, 2, 3, 4, 5, \ldots \quad \text{Equation 14:}$$

In this equation, the term $\delta_j(\lambda)$ is the position-dependent correction factor. It is a function to be determined by fitting the calculated $A_{ji}(\lambda)$ values to a polynomial function at multiple $\lambda$ positions. Assume the polynomial is a quadratic function, then it needs at least three $A_{ji}(\lambda)$ values at three different 2 positions.

Suppose the color calibration substance is running through X capillaries, at the same time or at different times, at positions $\lambda_1, \lambda_2, \ldots, \lambda_9$. Firstly, the color-bleed factors from N dyes can be averaged to enhance the accuracy as shown in Equation 15:

$$f_j(\lambda_k) = \sum_{i=1}^{5} A_{ji}(\lambda_k)/5 \text{ with } k = 1, 2, \ldots \quad \text{Equation 15}$$

The $f_j(\lambda_k)$ values are then used to fit the quadratic function of Equation 16:

$$g_j(\lambda)=a_{j0}+a_{j1}\lambda+a_{j2}\lambda^2. \quad \text{Equation 16:}$$

The fitting results, $a_{j0}$, $a_{j1}$, and $a_{j2}$, are the quadratic function coefficients for the term $(1+\delta_j(\lambda))$ in Equation 14. They are used to calculate for the color-bleed factors $A_{ji}(\lambda)$ according to Equation 14 as shown in Equations 17 and 18:

$$A_{ji}(0)=a_{j0}, \quad \text{Equation 17:}$$

and $$\delta_j(\lambda)=(a_{j1}/a_{j0})\lambda+(a_{j2}/a_{j0})\lambda^2. \quad \text{Equation 18:}$$

In addition to the dependence of the excitation position, the color-bleed factors may also vary with the DNA locus of the fragment. This should not occur for an ideal dye. However, the dye is attached to a primer, and the primer is specific for each locus. The chemical environment of the primer may affect the fluorescent spectrum of certain dyes. If the color-bleed factors for a locus differ significantly from that of other loci, then it is desirable to calculate the color-bleed factors specifically for that locus. This can be done by simply selecting and summing the peak areas only the fragments within the size range of the locus, and use them to calculate $Q_{ji}$ as shown in Equation 9. In this case, there are special sets of color-bleed factors, $A_{ji}(\lambda)$, prepared for these special loci. Each special set is used, according to the same Equation 6, for color separation of the signals within the fragment size range of the special locus.

The color calibration substance can be prepared in different forms. For example, it may contain fragments of only one dye and it is used to determine the color-bleed factors of this dye. In this way, it can have more fragments of this dye in the substance. However, another substance is needed to prepare and calculate the color-bleed factors for another dye. Likewise, one substance may contain fragments of two dyes and another substance contains fragments of other dyes. In a calibration procedure, these multiple substances can run simultaneously in separate capillaries of the same biochip.

However, for a routine DNA analysis, multiple substances for color calibration take away the sample space and which may not be desirable.

With respect to detector gain, the color-bleed factor $A_{ji}$ can be separated into two terms representing the two stages of the color-bleed process as shown in Equation 19:

$$A_{ji}=G_j^*\alpha_{ji}. \quad \text{Equation 19:}$$

The first term $\alpha_{ji}$ describes the combined effect of fluorescent spectrum and the filter characteristics. The second term, $G_j$, describes the optical detection and amplification. It can be considered as the gain of the detection channel. In terms of gain, color bleed can be represented as shown in Equation 20:

$$Y_j = G_j * \sum_{i=1}^{5} \alpha_{ji} X_i \text{ with } j = 1, 2, \ldots. \quad \text{Equation 20}$$

Due to variation of the gain over time, the gain changes to $G'_j$ at the run time, and the detected signal represented as shown in Equation 21:

$$Y_j = G'_j * \sum_{i=1}^{5} \alpha_{ji} X_i. \quad \text{Equation 21}$$

If the gain $G'_j$ is measured for each detection channel, it can be used to modify the color-bleed factors as shown in Equation 22:

$$A'_{ji}=G'_j{}^*\alpha_{ji}=(G'_j/G_j)^*A_{ji}. \quad \text{Equation 22:}$$

The modified matrix A' is then used to find the inverse matrix B, and the color-separated signal X can be calculated according to Equation 6.

This can be alternatively be expressed as shown in Equation 23:

$$(G_j/G'_j)*Y_j = \sum_{i=1}^{5} A_{ji} X_i. \quad \text{Equation 23}$$

The detected signal $Y_j$ is scaled as show in Equation 24:

$$Y'_j=(G_j/G'_j)^*Y_j. \quad \text{Equation 24:}$$

Follow Equations 5 and 6, the unknown $X_i$ can be calculated from the original color-bleed factors $A_{ji}$ as shown in Equation 25:

$$X_i = \sum_{j=1}^{5} B_{ij} Y'_j. \quad \text{Equation 25}$$

Using the relative gain $r_j$ for channel j, with respect to the gain of a reference channel, the ratio of the gains can be represented as shown in Equations 26 and 27:

$$r_j=G_j/G_1, \text{ and} \quad \text{Equation 26:}$$

$$r'_j=G'_j/G'_1. \quad \text{Equation 27:}$$

Using Equations 26 and 27, Equation 23 can be written as shown in Equation 28L $$(r_j/r'_j)*Y_j = (G'_1/G_1)*\sum_{i=1}^{5} A_{ji}X_i.$$

Equation 28

The detected signal is first scaled by the relative gain as shown in Equation 29:

$$Y'_j=(r_j/r'_j)*Y_j.$$

Equation 29:

$X'_i$ can be represented as show in Equation 30:

$$X'_i=(G'_1/G_1)*X_i.$$

Equation 30:

Using Equations 5 and 6, and the original color-bleed factors $A_{ji}$, renders Equation 31:

$$X'_i = \sum_{i=1}^{5} B_{ij}Y'_j.$$

Equation 31

The unknown $X_i$ can be calculated as shown in Equation 32:

$$X_i=(G_1/G'_1)*X'_i.$$

Equation 32:

This is just a constant scaling of a factor close to one for all color separated signals. It can be omitted, in which we just use $X'_i$ for $X_i$. If it is desirable to take account of this constant scaling, then it is preferred to scale the detected signal as shown in Equation 33:

$$Y'_j=(G_1/G'_1)*(r_j/r'_j)*Y_j.$$

Equation 33:

The unknown $X_i$ is then given by the result of the inverse matrix $B_{ij}$ multiplied by $Y'_j$.

In summary, in the calibration for the color-bleed factors $A_{ji}$, the ratio of the gain for every detection channel with respect to a reference channel is calculated and stored as $r_j$. During a run with DNA samples, the gains of all channels are measured and the relative gain $r'_j$ is calculated for every detection channel with respect to the same reference channel as in the calibration. These relative gains are used to scale detected signal before the color separation using the original color-bleed factors $A_{ji}$. The ratio of the reference channel gains, $G_1/G'_1$, can be used to scale the detected signal.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. A method, comprising:
generating a first signal indicative of a reference gain of optical detectors of a sample processing apparatus based on a first emission from a gain-monitoring material of the sample processing apparatus in response to illuminating the gain-monitoring material;
generating a second signal indicative of a subsequent gain of the optical detectors based on a second emission from a gain-monitoring material in response to illuminating the gain-monitoring material; and
scaling at least one of color bleed factors of the sample processing apparatus or data acquired by the sample processing apparatus based on a signal indicative of a difference between the reference gain and the subsequent gain.

2. The method of claim 1, wherein the second signal is determined at least one of before, during or after an acquisition time in which one or more DNA samples are processed by the sample processing.

3. The method of claim 1, wherein the gain-monitoring material is part of the sample processing apparatus.

4. The method of claim 1, wherein the gain-monitoring material is part of a sample carrier received by the sample processing apparatus, wherein the sample carrier includes one or more channels for carrying samples to be processed by the sample processing apparatus.

5. The method of claim 1, wherein the gain-monitoring material includes one or more fluorescent materials that have a known emission spectrum within a predetermined emission spectrum of interest.

6. The method of claim 1, wherein the gain-monitoring material is illuminated by a source of the sample processing apparatus used to illuminates separated DNA fragments.

7. The method of claim 1, wherein the gain-monitoring material is illuminated by a source of the sample processing apparatus that is different from a sample source used to illuminates separated DNA fragments.

8. An apparatus, comprising:
memory storing color bleed factors;
optical detectors; and
a processor configured to:
generate a first signal indicative of a reference gain of the optical detectors based on a first emission from a gain-monitoring material in response to illuminating the gain-monitoring material;
generate a second signal indicative of a subsequent gain of the optical detectors based on a second emission from a gain-monitoring material in response to illuminating the gain-monitoring material; and
scale at least one of the color bleed factors or acquired data based on a signal indicative of a difference between the reference gain and the subsequent gain.

9. The apparatus of claim 8, wherein the second signal is determined at least one of before, during or after an acquisition time in which one or more DNA samples are processed by the sample processing.

10. The apparatus of claim 8, wherein the gain-monitoring material is part of the apparatus.

11. The apparatus of claim 8, further comprising:
a sample carrier with one or more channels configured to carry samples, wherein the gain-monitoring material is part of the sample carrier.

12. The apparatus of claim 11, further comprising:
one or more fluorescent materials that have a known emission spectrum within a predetermined emission spectrum of interest, wherein the gain-monitoring material includes the one or more fluorescent materials.

13. The apparatus of claim 8, further comprising:
an illumination source configured to illuminate separated DNA fragments, wherein the illumination source illuminates the gain-monitoring material.

14. The apparatus of claim 8, further comprising:
a first illumination source configured to illuminate separated DNA fragments; and
a second illumination source configured to illuminate the gain-monitoring material, wherein the first and second illumination sources are different sources.

* * * * *